United States Patent [19]

Hoffmann et al.

[11] 4,358,409

[45] Nov. 9, 1982

[54] PREPARATION OF STYRYL CYCLOPROPANE INSECTICIDE INTERMEDIATES

[75] Inventors: Hellmut Hoffmann; Fritz Maurer, both of Wuppertal; Uwe Priesnitz, Unna-Massen; Hans-Jochem Riebel, Wuppertal, all of Fed. Rep. of Germany

[73] Assignee: Bayer Aktiengesellschaft, Leverkusen, Fed. Rep. of Germany

[21] Appl. No.: 140,644

[22] Filed: Apr. 16, 1980

[30] Foreign Application Priority Data

May 2, 1979 [DE] Fed. Rep. of Germany ....... 2917620
Jul. 21, 1979 [DE] Fed. Rep. of Germany ....... 2929636

[51] Int. Cl.³ ............... C07C 120/00; C07C 121/48; C07C 69/743; C07C 69/616
[52] U.S. Cl. .............................. 260/465 G; 585/641; 585/642; 260/464; 260/465 F; 260/465 K; 260/544 L; 260/940; 260/941; 260/943; 260/946; 260/953; 560/8; 560/17; 560/51; 560/61; 560/62; 560/63; 560/124; 562/405; 564/152; 564/161; 564/162; 564/169; 564/171; 564/190; 568/319; 568/322; 568/361; 570/199; 570/6; 585/437; 585/638; 585/639; 585/640
[58] Field of Search ................... 560/8, 51, 61, 62, 63, 560/17, 124; 260/465 D, 464, 465 F, 465 K, 465 G; 570/217; 585/437; 568/361, 322; 564/190, 152, 162, 169, 161, 171

[56] References Cited

U.S. PATENT DOCUMENTS 3,818,030 6/1974 Timmler et al. ................ 260/953 X

FOREIGN PATENT DOCUMENTS 2738150 3/1980 Fed. Rep. of Germany .

OTHER PUBLICATIONS

Fieser and Fieser; Reagents for Organic Synthesis; vol. 1, (1967), pp. 250, 1138, 1212.
Fieser and Fieser; Reagents for Organic Synthesis; vol. 2, (1969), pp. 60, 130, 131, 132, 181, 271, 432, 442, 457.
Fieser and Fieser; Reagents for Organic Synthesis; vol. 3, (1972), pp. 94, 97, 141, 142, 146.
Fieser and Fieser; Reagents for Organic Synthesis; vol. 4, (1974), pp. 83, 550, 573.
Fieser and Fieser; Reagents for Organic Synthesis; vol. 5, (1975), pp. 30, 209.
Fieser and Fieser; Reagents for Organic Synthesis; vol. 6, (1977), p. 14.
Fieser and Fieser; Reagents for Organic Synthesis; vol. 7, (1979), pp. 97, 160.
Horner, et al., Ber., *103*, (1970), pp. 2984–2986.
Matsuo, et al., Tetrahedron Letters, *23*, (1976), pp. 1979–1982.

Primary Examiner—Joseph Paul Brust
Attorney, Agent, or Firm—Sprung, Horn, Kramer & Woods

[57] ABSTRACT

Styryl-cyclopropane derivatives of the formula

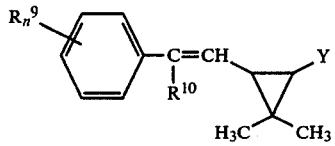

in which $R^9$ represents independently of one another when n=2, halogen, cyano, nitro, or an optionally halogen-substituted alkyl, alkoxy, alkylthio or alkylenedioxy radical, n represents zero, 1, 2, 3, 4 or 5, $R^{10}$ represents hydrogen or halogen and Y represents acetyl, cyano or carbamoyl, are produced by reacting a benzylphosphonic acid ester of the formula

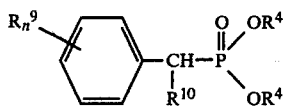

in which $R^4$ each independently represents alkyl or phenyl or together represent alkylene, with a formylcyclopropane derivative of the formula

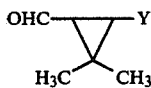

or by reacting an α-hydroxyphosphonic acid ester of the formula

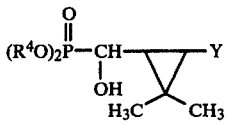

with an olefinating agent of the formula

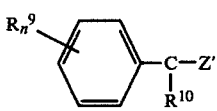

in which Z' represents a phosphorus-containing radical

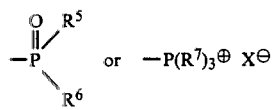

wherein
R$^5$ and R$^6$ are identical or different and individually represent alkyl, phenyl, alkoxy or pehnoxy or R$^5$ and R$^6$ together represent alkanedioxy,
R$^7$ represents alkyl or phenyl and
X represents halogen, in the presence of a base at a temperature between about $-70°$ and $+150°$ C. Other olefins can be similarly prepared. Many intermediates are new and the end products are themselves intermediates for insecticides.

8 Claims, No Drawings

PREPARATION OF STYRYL CYCLOPROPANE INSECTICIDE INTERMEDIATES

The invention relates to an unobvious process for the preparation of certain alkenes, some of which are known, to certain new styryl cyclopropane derivatives which can be prepared by this process and by other processes, and to intermediate products for the preparation of said alkenes.

It is known that such alkenes as, for example, 3-(2-methyl-2-methoxy-carbonyl-vinyl)-2,2-dimethyl-cyclopropane-1-carboxylic acid tert.-butyl ester, which can be used as an intermediate product for insecticidally active pyrethroids, are obtained when aldehydes or ketones, for example 3-formyl-2,2-dimethyl-cyclopropane-2-carboxylic acid tert.-butyl ester, are reacted with phosphorus-ylides (phosphorus-ylenes), for example (1-methoxy-carbonylethylidene)-phosphonic acid diethyl ester (see Organic Reactions, Volume 25 (1977), page 73–253, in particular page 85 and page 121, and the literature quoted there).

It is also known, as a special case of the abovementioned synthesis method, that certain 3-(2-chloro-2-phenyl-vinyl)-2,2-dimethyl-cyclopropane-1-carboxylic acid esters, for example 3-(2-chloro-2-phenyl-vinyl)-2,2-dimethyl-cyclopropane-1-carboxylic acid ethyl ester, are obtained when corresponding benzyl-phosphonic acid esters are treated with a strong base, for example butyl-lithium, and the ylides intermediately formed are reacted with carbon tetrachloride and then with 3-formyl-2,2-dimethyl-cyclopropane-1-carboxylic acid esters (see DE-OS (German Published Specification) No. 2,738,150).

The carbonyl olefination reaction described in general terms above indeed has a very broad applicability, but is of no further interest for industrial purposes, for example, if the aldehydes (or ketones) to be employed as starting substances can be prepared only at very great expense. Thus, according to the state of the art, the 3-formyl-2,2-dimethyl-cyclopropane-1-carboxylic acid esters which can be used as intermediate products for pyrethroids are obtained by ozonolysis of 3-alkenyl-2,2-dimethyl-cyclopropane-1-carboxylic acid esters, for example chrysanthemic acid ethyl ester, which in turn can be prepared from naturally occurring pyrethroids (see U.S. Pat. No. 3,679,667). A preparative method for 3-formyl-2,2-dimethyl-cyclopropane-1-carboxylic acid esters which is simple to carry out industrially is not known.

To carry out the known method described above for the synthesis of 3-(2-chloro-2-phenyl-vinyl)-2,2-dimethyl-cyclopropane-1-carboxylic acid esters industrially would necessitate a high expenditure:

The strong bases, for example butyl-lithium, required for ylide formation from benzylphosphonic acid esters are sensitive to moisture and air; the reaction is thus carried out in an inert gas atmosphere, for example under nitrogen or argon, and using an inert, carefully dried diluent. Since the reaction has to be carried out at a low temperature, for example at −70° C., the reaction mixture must also be cooled intensively. Working up of the mixture to isolate the desired products, which are obtained as isomer mixtures, is likewise expensive; it comprises several extractions and solvent distillations and a chromatographic separation process. For these reasons, the known synthesis method is not very suitable for preparing 3-(2-chloro-2-phenyl-vinyl)-2,2-dimethyl-cyclopropane-1-carboxylic acid esters on an industrial scale.

The present invention now provides:

(1) a process for the preparation of an alkene of the general formula

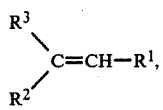

in which

R$^1$ represents an optionally substituted alkyl, alkenyl, alkynyl, cycloalkyl, cycloalkenyl, aralkyl, aralkenyl or aryl radical or an optionally substituted heterocyclic radical, R$^2$ represents hydrogen or halogen and R$^3$ represents halogen, cyano, an optionally substituted alkyl, alkenyl, alkynyl, cycloalkyl, aralkenyl, aryl, alkylcarbonyl, arylcarbonyl, alkoxycarbonyl or aminocarbonyl radical or an optionally substituted heterocyclic radical, characterized in that an α-hydroxy-phosphonic acid ester of the general formula

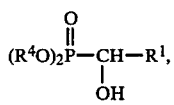

in which

R$^1$ has the meaning indicated above and

R$^4$ represents alkyl or phenyl, or the two radicals R$^4$ together represent straight-chain or branched alkanediyl (alkylene), is reacted with a phosphorus-containing olefinating agent of the general formula

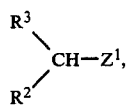

in which

R$^2$ and R$^3$ have the meanings indicated above and

Z$^1$ represents a phosphorus-containing radical

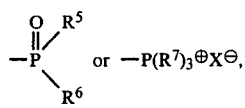

wherein

R$^5$ and R$^6$ are identical or different and individually represent alkyl, phenyl, alkoxy or phenoxy, or R$^5$ and R$^6$ together represent alkanedioxy, R$^7$ represents alkyl or phenyl and X represents halogen, in the presence of a base, if appropriate in the presence of a catalyst and if appropriate using a diluent, at a temperature between about −70 and +150 C.;

(2), as new compounds, the α-hydroxy-phosphonic acid esters of the general formula

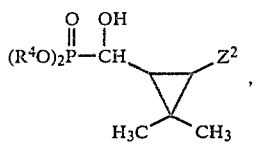 (IIa)

in which
R$^4$ represents alkyl or phenyl or the two radicals R$^4$ together represent straight-chain or branched alkanediyl (alkylene) and
Z$^2$ represents cyano, carbamoyl, acetyl or C$_1$–C$_4$-alkoxycarbonyl;

(3) a process for the preparation of an α-hydroxy-phosphonic acid ester of the formula (IIa) above, characterized in that an α-oxo-phosphonic acid ester of the general formula

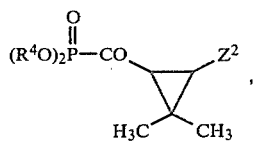 (IV)

in which
R$^4$ and Z$^2$ have the meanings indicated under (2), is reacted with a hydride complex of the general formula

 M(M'H$_4$) (V), in which
M represents lithium, sodium or potassium and
M' represents boron or aluminum, if appropriate in the presence of a buffer and if appropriate using a diluent, at a temperature between about −20 and +50 C.;

(4) as new compounds, the α-oxo-phosphonic acid esters of the general formula

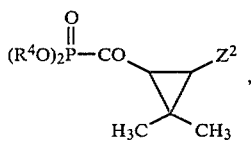 (IV)

in which
R$^4$ represents alkyl or phenyl or the two radicals R$^4$ together represent straight chain or branched alkanedyl (alkylene) and
Z$^2$ represents cyano, carbamoyl, acetyl or C$_1$–C$_4$-alkoxycarbonyl;

(5) a process for the preparation of an α-oxo-phosphonic acid ester of the formula (IV) above, characterised in that a carboxylic acid chloride of the general formula

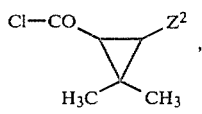 (VI)

in which

Z$^2$ has the meaning indicated under (4), is reacted with a phosphorous acid ester of the general formula

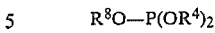 R$^8$O—P(OR$^4$)$_2$ (VII), in which
R$^4$ has the meaning indicated under (4) and
R$^8$ represents methyl or ethyl, at a temperaure between about −20 and +150 C.;

(6) as new compounds, the carboxylic acid chlorides of the general formula

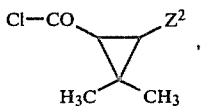 (VI)

in which
Z$^2$ represents cyano, carbamoyl, acetyl or C$_1$–C$_4$-alkoxycarbonyl; and (7) a process for the preparation of a carboxylic acid chloride of the formula (VI) above, characterized in that a carboxylic acid of the general formula

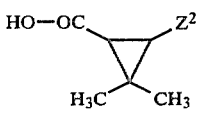 (VII)

in which
Z$^2$ has the meaning indicated under (6), is reacted with a chlorinating agent at a temperature between about 20 and 80 C.

The present invention furthermore provides:

(8) as new compounds, the styryl-cyclopropane derivatives of the general formula

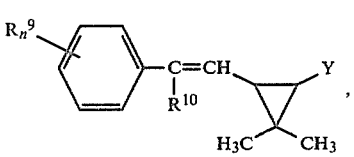 (XI)

in which
R$^9$ represents, independently of one another when n≧2, halogen, an optionally halogen-substituted alkyl, alkoxy, alkylthio or alkylenedioxy radical, or cyano or nitro,
n represents zero, 1, 2, 3, 4 or 5,
R$^{10}$ represents hydrogen or halogen and
Y represents acetyl, cyano or carbamoyl;

(9) a process for the preparation of a styryl-cyclopropane derivative of the formula (XI) above, characterized in that a benzylphosphonic acid ester of the general formula

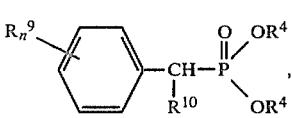 (XII)

in which
R$^9$, n and R$^{10}$ have the meanings indicated under (8) and the radicals $R^4$ individually represent alkyl or phenyl or together represent alkanediyl (alkylene), is reacted with a formyl-cyclopropane derivative of the general formula

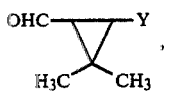   (XIII)

in which Y has the meaning indicated above, in the presence of a base and if appropriate using a diluent, at a temperature between about $-70$ and $+150$ C.;

(10) as new compounds, the formyl-cyclopropane derivatives of the general formula

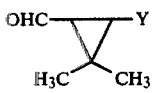   (XIII)

in which Y represents acetyl or carbamoyl;

(11) a process for the preparation of the formyl-cyclopropane derivative of the formula (XIII) above, in which Y represents acetyl, characterized in that 2-acetyl-3,3-dimethyl-cyclopropane-1-carboxylic acid chloride of the formula

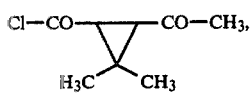   (XIV)

is reacted with lithium tri-tert.-butoxy-hydrido-aluminate, if appropriate using a diluent, at a temperature between about $-100°$ and $+100°$ C.; and

(12) a process for the preparation of a formyl-cyclopropane derivative of the formula (XIII) above, in which Y represents acetyl, cyano or carbamoyl, characterized in that an α-hydroxy-cyclopropylmethyl-phosphonic acid ester of the general formula

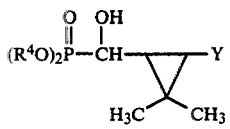   (XV)

in which $R^4$ represents alkyl or phenyl or the two radicals $R^4$ together represent alkanediyl (alkylene) and Y represents acetyl, cyano or carbamoyl, is reacted with an aqueous alkali metal hydroxide solution, if appropriate in the presence of a water-immiscible organic solvent, for example methylene chloride, at a temperature between about 0 and 100 C.

Surprisingly, alkenes of the formula (I) can be obtained in good yields and in high purity by the new process (1) above, which is simple and inexpensive to carry out and for which starting compounds which can be prepared without great expense are to be employed.

Advantages of the new process include, for example, the possibility of carrying out the reaction at room temperature or at least at temperatures which do not deviate far from this temperature, of using cheap bases, such as alkali metal hydroxides or alcoholates, and of employing water-containing solvents.

A particular advantage of the process according to the invention is that it is possible to avoid the preparation of aldehydes, which are in general employed as reactants in the preparation of alkenes by reaction of carbonyl compounds with phosphorus-containing olefinating agents.

If, for example, α-(3-methoxy-carbonyl-2,2-dimethyl-cycloprop-1-yl)-α-hydroxymethane-phosphonic acid dimethyl ester and α-chlorobenzylphosphonic acid diethyl ester are used as starting substances in process (1), the reaction of those compounds can be outlined by the following equation:

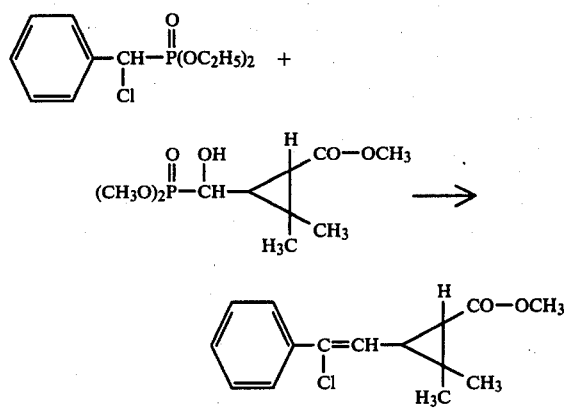

Formula (II) provides a definition of the α-hydroxyphosphonic acid esters to be used as starting substances. Preferably, in this formula, $R^4$ represents $C_1$–$C_4$-alkyl or phenyl, or the two radicals $R^4$ together represent 2,2-dimethyl-propane-1,3-diyl and $R^1$ represents optionally halogen-substituted $C_1$–$C_4$-alkyl, $C_3$–$C_6$-cycloalkyl which optionally carries one or more substituants selected from halogen, cyano, carbamoyl, $C_1$–$C_4$-alkyl, $C_1$–$C_4$-alkyl-carbonyl, $C_1$–$C_4$-alkoxy-carbonyl and phenoxybenzyloxy-carbonyl, the last-mentioned group being itself optionally substituted by fluorine and/or by cyano and/or by ethinyl, benzyl or phenylethyl, either of which is optionally substituted by chlorine, or phenyl which is optionally substituted by halogen and/or by $C_1$–$C_4$-alkyl and/or by $C_1$–$C_4$-alkoxy.

A particularly preferred group of new starting compounds of the formula (II) are those in which $R^1$ represents the radical

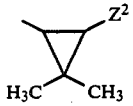

wherein $Z^2$ represents cyano, carbamoyl, acetyl or $C_1$–$C_4$-alkoxycarbonyl and $R^4$ represents methyl or ethyl.

Examples of the compounds (II) which may be mentioned are: α-hydroxy-3-methyl-benzyl-, α-hydroxy-4-methyl-benzyl-, α-hydroxy-3,4-dimethyl-benzyl-, α-hydroxy-4-fluoro-benzyl-, α-hydroxy-3-chloro-benzyl-, α-hydroxy-4-chloro-benzyl-, α-hydroxy-3,4-dichloro-benzyl-, α-hydroxy-3-bromo-benzyl, α-hydroxy-4- bromo-benzyl-, α-hydroxy-4-methoxy-benzyl- and α-hydroxy-3,4-dimethoxy-benzyl-phosphonic acid dimethyl ester and diethyl ester, α-hydroxy-α-(3-methoxy-carbonyl-2,2-dimethyl-cycloprop-1-yl)-methanephosphonic acid dimethyl ester and diethyl ester, α-hydroxy-α-(3-ethoxycarbonyl-2,2-dimethyl-cycloprop-1-yl)-methanephosphonic acid dimethyl ester and diethyl ester, α-hydroxy-α-(3-acetyl-2,2-dimethyl-cycloprop-1-yl)-methanephosphonic acid dimethyl ester and diethyl ester and α-hydroxy-α-(3-cyano-2, 2-dimethyl-cycloprop-1-yl)-methanephosphonic acid dimethyl ester and diethyl ester.

Some of the starting compounds of the formula (II) have not hitherto been described in the literature, but they can be prepared by processes which are known in principle. Thus, the new α-hydroxy-methane-phosphonic acid esters of the formula (IIa) are obtained by reacting the corresponding oxo compounds of the formula (IV) above with a reducing agent of the formula (V) above, for example sodium tetrahydridoborate (sodium boranate), if appropriate using a diluent, for example water or aqueous methanol, at a temperature between −20° and +50° C., preferably between −10° and +30° C., and by keeping the pH value between 5 and 8 by adding a buffer, for example sodium hydrogen phosphate (see Chem. Ber. 103 (1970), 2983–2986). For working up and isolation of the products, the mixture is extracted with a water-immiscible solvent, for example methylene chloride, the organic phase is dried and filtered and the solvent is distilled off from the filtrate under reduced pressure.

The substituted α-oxo-methanephosphonic acid esters of the formula (IV) have not been described before in the literature. These compounds are obtained by reacting carboxylic acid chlorides of the formula (VI) above with phosphorous acid esters of the formula (VII) above at a temperature between −20° and +150° C., preferably between 0° and 120° C. (see J. Am. Chem. Soc. 86 (1964), 3862–3866 and Methoden der organischen Chemie (Methods of Organic Chemistry) (Houben-Weyl-Müller), 4th. edition, Volume 12/1, page 453, Georg-Thieme Verlag, Stuttgart 1963).

For isolation and purification of the products, the mixture is distilled, if appropriate under reduced pressure.

An alternative route for the preparation of some of the compounds of the formula (II)-see formula (VIII)-is described below.

The cyclopropanecarboxylic acid chlorides of the formula (VI), which have not hitherto been described in the literature, are obtained from known cyclopropane-carboxylic acid esters according to the equation below (see J. Am. Chem. Soc. 89 (1967), 3912–3914; J. Org. Chem. 32 (1967), 3351–3355; Tetrahedron Lett. 1978, 1847–1850; and Bull. Soc. Chim. Belg. 87 (1978), 721–732) by methods which are in themselves known, by first preparing the corresponding cyclopropanecarboxylic acids by hydrolysis, for example by reaction with aqueous-alcoholic potassium hydroxide solution at temperatures between 20° and 100° C., and subsequent acidification, and reacting those acids with halogenating agents, for example thionyl chloride, at a temperature between 20° and 80° C.

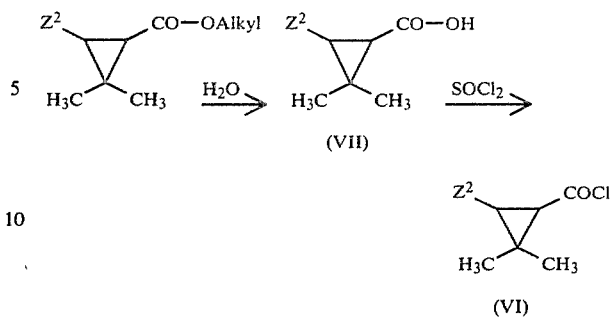

Formula (III) provides a definition of the phosphorus-containing olefinating agents also to be used as starting substances in process (1). Preferably, in this formula $R^2$ represents hydrogen, chlorine or bromine,
$R^3$ represents phenyl, which optionally carries one or more substituents selected from halogen, $C_1$–$C_4$-alkyl, $C_1$–$C_2$-halogeno-alkyl, $C_1$–$C_4$-alkoxy, $C_1$–$C_2$-halogenoalkoxy, $C_1$–$C_2$-(halo)alkylenedioxy, $C_1$–$C_4$-alkylthio and $C_1$–$C_2$-halogenoalkylthio, and
$Z^1$ represents the radical

wherein
$R^5$ and $R^6$ are identical or different and individually represent $C_1$–$C_4$-alkoxy or phenoxy or together represent 2,2-dimethyl-propane-1,3-dioxy.

Example of the compounds (III) which may be mentioned are: benzylphosphonic acid dimethyl ester and diethyl ester, α-chloro-benzylphosphonic acid dimethyl ester and diethyl ester, α-bromo-benzylphosphonic acid dimethyl ester and diethyl ester, 4-fluoro-, 3-chloro, 4-chloro-, 3,4-dichloro-, 3-bromo-, 4-bromo, 3-methyl-, 4-methyl-, 3,4-dimethyl-, 4-methoxy- and 3,4-dimethoxy-benzylphosphonic acid dimethyl ester and diethyl ester; 4-fluoro-, 4-chloro-, 3-chloro-, 3,4-dichloro-, 3-bromo-, 4-bromo-, 3-methyl-, 4-methyl-, 3,4-dimethyl-, 4-methoxy- and 3,4-dimethoxy-α-chloro-benzylphosphonic acid dimethyl ester and diethyl ester; and 4-fluoro-, 3-chloro-, 4-chloro-, 3,4-dichloro-, 3-bromo-, 4-bromo-, 3-methyl-, 4-methyl-, 3,4-dimethyl-, 4-methoxy- and 3,4-dimethoxy-α-bromo-benzylphosphonic acid dimethyl ester and diethyl ester.

Some of the phosphorus-containing olefinating agents of the formula (III) have not before been described in the literature, but they can be prepared by processes which are known in principle.

Benzylphosphonic acid esters which are unsubstituted in the α-position and fall within formula (III) are obtained by reacting benzyl halides with esters of phosphorous acid (see Methoden der organischen Chemie (Methods of Organic Chemistry) (Houben-Weyl-Müller), 4th edition, Volume 12/1, pages 433–453, Georg-Thieme-Verlag, Stuttgart (1963).

α-Chloro- and α-bromo-benzylphosphonic acid esters falling within formula (III) are obtained by reacting α-hydroxy-benzylphosphonic acid esters of the general formula

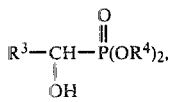

in which

R⁴ has the meaning indicated above and

R³ represents optionally substituted phenyl, with a chlorinating agent, for example thionyl chloride, or with a brominating agent, for example dibromotriphenylphosphorane, if appropriate in the presence of an acid acceptor, for example pyridine, and if appropriate using a diluent, for example methylene chloride or ethylene chloride, at a temperature between 10° and 100° C. or between −50° and +50° C. (see J. Am. Chem. Soc. 87(1965), 2777–2778; and Chimia 28 (1974), 656–657).

Some of the α-hydroxy-benzylphosphonic acid esters of the formula (VIII) have not been described in the literature. They are obtained by the route indicated above for the preparation of compounds of the formula (II), or by reacting benzaldehydes of the general formula

in which

R³ has the meaning indicated above, with phosphorous acid esters of the general formula

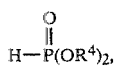

R⁴ has the meaning indicated above, if appropriate in the presence of a catalyst, for example triethylamine, at temperatures between 0° and 150° C., preferably between 20° and 100° C. (see Methoden der organischen Chemie (Methods of Organic Chemistry) (Houben-Weyl-Müller), 4th edition, Volume 12/1, pages 475–483, George-Thieme-Verlag, Stuttgart 1963).

The aldehydes of the formula (IX) and the phosphorous acid esters of the formula (X) are widely known.

The process according to the invention for the preparation of alkenes of the formula (I) is preferably carried out using a suitable solvent or diluent. Possible solvents or diluents are, in addition to water, virtually any of the inert organic solvents. These include, as preferences, aliphatic and aromatic, optionally chlorinated hydrocarbons, such as pentane, hexane, heptane, cyclohexane, benzene, toluene, xylene, methylene chloride, ethylene chloride, chloroform, carbon tetrachloride, chlorobenzene and dichlorobenzenes; ethers, such as diethyl ether, dibutyl ether, tetrahydrofuran and dioxane; alcohols, such as methanol, ethanol, n- and iso-propanol and n-, iso-, sec.- and tert.- butanol; and aprotic polar solvents, such a dimethylformamide and dimethylsulphoxide. When the reaction is carried out in a two-phase medium, an organic solvent, such as pentane, hexane, heptane, benzene or toluene, which is water-immiscible is used, in general in addition to about 50% strength sodium hydroxide solution or potassium hydroxide solution.

Catalysts which are used, when the process according to the invention is carried out in multi-phase reaction media, are compounds which are customarily used as auxiliaries for the phase transfer of reactants in reactions in multi-phase systems. Tetraalkyl-and trialkyl-benzyl-ammonium salts, for example tetrabutylammonium bromide and trimethylbenzyl-ammonium chloride, may be mentioned as such phase transfer catalysts.

Bases which can be used in carrying out the process according to the invention are the bases customarily used for carbonyl olefination reactions. Bases which may be mentioned are alkali metal hydroxides, for example potassium hydroxide and sodium hydroxide; alkali metal alcoholates, for example potassium methylate, ethylate, n-and iso-propylate and n-, iso-, sec.- and tert.-butylate and sodium methylate, ethylate, n- and iso-propylate and n-, iso-, sec.- and tert.-butylate; alkali metal hydrides, for example sodium hydride; and alkyl-lithium compounds, for example butyl-lithium. The alkali metal hydroxides and/or alcoholates mentioned are preferably used.

The process is in general carried out under normal pressure. The reaction temperatures are between −70° and +150° C., preferably between −20° and +50° C.

The starting compounds of the formulae(II) and (III) are usually employed in equimolar amounts for carrying out the process according to the invention. When the process is carried out in a one-phase system, two equivalents of base are in general used; when 50% strength alkali metal hydroxide solutions are used as second phases, 5 to 15 times the stoichiometrically required amount is in general employed.

The base, and, if appropriate, the catalyst are initially introduced in a suitable reaction medium and the starting substances of the formulae (II) and (III)—if appropriate dissolved in one of the solvents indicated— are simultaneously or successively added to the mixture. The mixture is stirred for several hours to bring the reaction to completion.

The mixture can be worked up by customary methods. To isolate products which can be distilled, for example, the solvent can be distilled off, the residue can be taken up in a water-immiscible solvent, for example ligroin, the solution can be washed, dried and filtered and the filtrate can be distilled. To isolate crystalline products, if appropriate the reaction mixture can be poured into water or ice-water and the crystalline product can be filtered off. If the solvent is not water-miscible, the reaction mixture can be washed with water, dried and filtered and the filtrate can be evaporated. It is also possible for oily products which are difficult to distil to be obtained in a relatively pure form by the latter method of working up.

The products are characterized by their melting points or boiling points.

Compounds of the formula (I) which can be prepared by the process according to the invention can be used as intermediate products for the preparation of insecticides (see DE-OS (German Published Specification) No. 2,738,150).

As already mentioned, the new alkenes of the formula (XI) can be prepared by the new process (I) above. However, these new compounds can also be prepared by process (9) above.

If, for example, α-chloro-benzyl-phosphonic acid dimethyl ester and 2-formyl-3,3-dimethyl-cyclopropane-1-carboxylic acid amide are used as the starting substances and sodium hydroxide is used as the base in process (9), the reaction of these compounds can be outlined by the following equation:

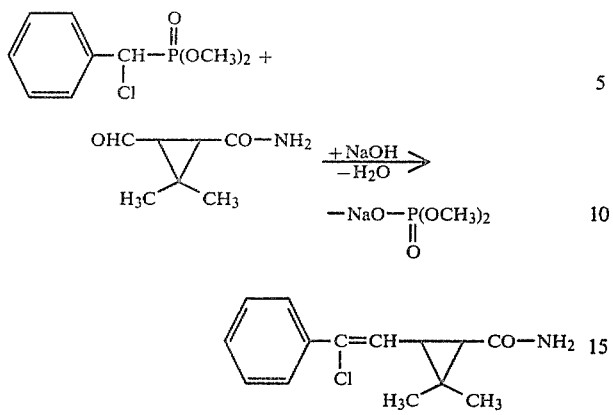

The new styryl-cyclopropane derivatives of the formula (XI) that are preferably obtained are those in which $R^9$ represents fluorine, chlorine, bromine, $C_1$-$C_4$-alkyl, trifluoromethyl, $C_1$-$C_4$-alkoxy, $C_1$-$C_2$-fluoroalkoxy, $C_1$-$C_2$-chlorofluoroalkoxy, $C_1$-$C_4$-alkylthio, $C_1$-$C_2$-fluoroalkylthio, $C_1$-$C_2$-chlorofluoroalkylthio, $C_1$-$C_2$-alkylenedioxy, $C_1$-$C_2$-fluoroalkylenedioxy, cyano or nitro, n represents zero, 1, 2, 3, 4 or 5, $R^{10}$ represents hydrogen, chlorine or bromine, and Y represents acetyl, cyano or carbamoyl.

The process described under (9) above is preferably carried out using a diluent.

Preferred diluents are polar organic solvents. These include carboxylic acid amides, for example dimethylformamide and N-methyl-pyrrolidone; sulphoxides and sulphones, for example dimethylsulphoxide and tetramethylene sulphone; phosphoric acid amides, for example hexamethylphosphoric acid triamide; ethers, for example glycol dimethyl ether, diglycol dimethyl ether, tetrahydrofuran and dioxane; nitriles, for example acetonitrile and propionitrile; and alcohols, for example methanol, ethanol, n- and iso-propanol and n-, iso-, sec.- and tert.-butanol.

Any of the bases customary in carbonyl olefination reactions can be used in process (9). Bases which may be mentioned are alkali metal hydroxides, for example sodium hydroxide and potassium hydroxide; alkali metal alcoholates, for example sodium methylate, ethylate, n- and iso-propylate and n-, iso-, sec.- and tert.-butylate and potassium methylate, ethylate, n- and iso-propylate and n-, iso-, sec.- and tert.-butylate; alkali metal hydrides, for example sodium hydride; and alkyllithium compounds, for example butyl-lithium. Alcoholates are the particularly preferred bases.

The reaction temperatures are in general from $-70°$ to $+150°$ C., preferably from $-20°$ to $+50°$ C. The process is in general carried out under normal pressure.

The starting compounds of the formulae (XII) and (XIII) are generally employed in equimolar amounts.

In a preferred embodiment of process (9), the base is initially introduced in one of the diluents indicated above, and a benzylphosphonic acid ester of the formula (XII) and a formyl-cyclopropane derivative of the formula (XIII) are successively added dropwise. The reaction mixture is stirred for several hours and worked up by one of the customary methods; the mixture is diluted with water and extracted with a water-immiscible solvent, for example methylene chloride or toluene, the extract is dried and filtered and the solvent is distilled off from the filtrate. The crude product which remains can be purified by vacuum distillation. The boiling point and/or refractive index are used for its characterization.

Formula (XII) provides a definition of the benzylphosphonic acid esters to be used as starting substances in process (9). Preferably, in this formula, $R^9$ and $R^{10}$ represent those radicals which have already been mentioned as preferred in the case of the definition of the radicals $R^9$ and $R^{10}$ in formula (XI), n represents zero, 1, 2, 3, 4 or 5 and $R^4$ represents $C_1$-$C_4$-alkyl or phenyl, or the two radicals $R^4$ together represent 2,2-dimethyl-propane-1,3-diyl.

Examples of the compounds (XII) which may be mentioned are: benzylphosphonic acid dimethyl ester and diethyl ester, α-chloro-benzylphosphonic acid dimethyl ester and diethyl ester, α-bromo-benzylphosphonic acid dimethyl ester and diethyl ester, 4-fluoro-, 3-chloro-, 4-chloro-, 3,4-dichloro-, 3-bromo-, 4-bromo-, 3-methyl-, 4-methyl-, 3,4-dimethyl-, 4-methoxy- and 3,4-dimethoxy-benzylphosphonic acid dimethyl ester and diethyl ester; 4-fluoro-, 4-chloro-, 3-chloro-, 3,4-dichloro-, 3-bromo-, 4-bromo-, 3-methyl-, 4-methyl-, 3,4-dimethyl-, 4-methoxy- and 3,4-dimethoxy-α-chlorobenzylphosphonic acid dimethyl ester and diethyl ester, 4-fluoro-, 3-chloro-, 4-chloro-, 3,4-dichloro-, 3-bromo-, 4-bromo-, 3-methyl-, 4-methyl-, 3,4-dimethyl-, 4-methoxy- and 3,4-dimethoxy-α-bromo-benzylphosphonic acid dimethyl ester and diethyl ester. Some of the benzyl-phosphonic acid esters of the formula (XII) have not hitherto been described in the literature, but they can be prepared by processes which are known in principle.

Benzylphosphonic acid esters of the formula (XII) in which $R^{10}$ represents hydrogen are obtained by reacting corresponding benzyl halides with esters of phosphorous acid (see Methoden der organischen Chemie (Methods of Organic Chemistry) (Houben-Weyl-Müller), 4th edition, Volume 12/1, pages 433–453, Georg-Thieme-Verlag, Stuttgart 1963).

Benzyl-phosphonic acid esters of the formula (XII) in which $R^{10}$ represents chlorine or bromine are obtained by reacting α-hydroxy-benzylphosphonic acid esters of the general formula

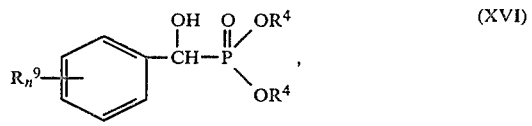

in which $R^9$, n and $R^4$ have the meanings indicated above, with a chlorinating agent, for example thionyl chloride, or with a brominating agent, for example dibromotriphenylphosphorane, if appropriate in the presence of an acid acceptor, for example pyridine, and if appropriate using a diluent, for example methylene chloride or ethylene chloride, at a temperature between $-50°$ and $+50°$ C. (see J. Am. Chem. Soc. 87 (1965), 2777–2778; and Chimia 28 (1974), 656–657).

α-Hydroxy-benzylphosphonic acid esters of the formula (XVI) are obtained by reacting benzaldehydes of the general formula

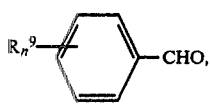 (XVII)

in which
R$^9$ and n have the meanings indicated above, with phosphorous acid esters of the formula

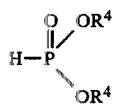 (XVIII)

in which
R$^4$ has the meaning indicated above, if appropriate in the presence of a catalyst, for example triethylamine, at a temperature between 10° and 100° C. (see Methoden der organischen Chemie (Methods of Organic Chemistry) (Houben-Weyl-Müller), 4th edition, Volume 12/1, pages 475–483; George-Thieme-Verlag, Stuttgart 1963).

Aldehydes of the formula (XVII) and phosphoric acid esters of the formula (XVIII) are known.

Examples which may be mentioned of the formylcyclopropane derivatives of the formula (XIII) which are also to be used as starting compounds in process (9) are: 2-acetyl-3,3-dimethyl-cyclopropane-1-carbaldehyde, 2-cyano-3,3-dimethyl-cyclopropane-1-carbaldehyde and 2-carbamoyl-3,3-dimethyl-cyclopropane-1-carbaldehyde.

2-Acetyl-3,3-dimethyl-cyclopropane-1-carbaldehyde is obtained, for example, by the process indicated under (11), by reacting 2-acetyl-3,3-dimethyl-cyclopropane-1-carboxylic acid chloride (XIV) with lithium tri-tert.-butoxy-hydrido-aluminate (which, if appropriate, has been prepared in situ from lithium tetrahydrido-aluminate (lithium alanate) and tert.-butanol) if appropriate in the presence of a diluent, for example tetrahydrofuran, at a temperature between −100° and +100° C., preferably between −80° and +50° C. Working up can be effected by customary methods, for example by pouring the reaction mixture into a mixture of hydrochloric acid and ice-water, extracting the mixture with a water-immiscible solvent, for example diethyl ether, drying and filtering the extracts and concentrating the filtrate. If appropriate, the crude product which remains is purified by distillation.

In general terms, formyl-cyclopropane derivatives of the formula (XIII) are obtained by the process indicated under (12), by reacting α-hydroxycyclopropylmethyl-phosphonic acid esters of the formula (XV) above with aqueous alkali metal hydroxide solutions, for example with aqueous sodium hydroxide solution, if appropriate in the presence of a water-immiscible solvent, for example methylene chloride, at a temperature between 0° and 100° C., preferably between 10° and 50° C. (see Chem. Ber. 103 (1979), 2984–2986).

For working up, the organic phase is separated off, dried and filtered, the filtrate is concentrated and the crude product which remains in the residue is purified, if appropriate, by distillation.

α-Hydroxyphosphonic acid esters of the formula (XV) are obtained, for example, according to the equation below, starting from known cyclopropane-carboxylic acid esters of the formula (XIX), by saponifying these to give the corresponding acids of the formula (XVIII), preparing the acid chlorides of the formula (XVII) from these acids, producing the cyclopropanoyl-phosphonic acid esters of the formula (XVI) by reaction of the chlorides with alkyl phosphites and reducing these esters with sodium tetrahydridoborate (R$^{11}$ represents C$_1$–C$_4$-alkyl):

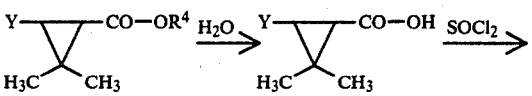

(XIX)     (XVIII)

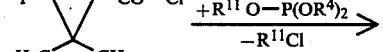

(XVII)

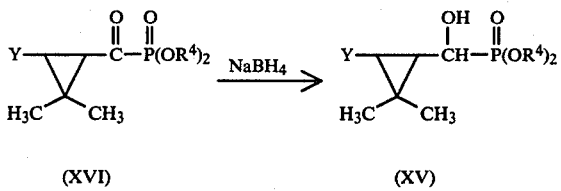

          

(XVI)     (XV)

The carboxylic acids of the formula (XVIII) are obtained by hydrolysis of known cyclopropanecarboxylic acid esters of the formula (XIX) (see J. Org. Chem. 32, (1967), 3351–3355; Bull. Soc. Chim. Belg. 87 (1978), 721–732; Tetrahedron Lett. 1978, 1847–1850), for example by reaction with aqueous-alcoholic potassium hydroxide solution at temperatures between 20° and 100° C. and subsequent acidification. These acids can be converted into the acid chlorides of the formula (XVII) by reaction with halogenating agents, for example thionyl chloride, at a temperature between 20° and 100° C.

The cyclopropanoylphosphonic acid esters of the formula (XVI) are obtained by reacting the acid chlorides (XVII) with alkyl phosphites at a temperature between −20° and +150° C., preferably between 0° and 100° C. (see J. Am. Chem. Soc. 86 (1964), 3862–3866; and Methoden der organischen Chemie (Methods of Organic Chemistry) (Houben-Weyl-Müller), 4th edition, Volume 12/1, page 453, Georg-Thieme-Verlag, Stuttgart 1963). Isolation and purification of the products is effected, if appropriate, by distillation under reduced pressure.

The α-hydroxy-phosphonic acid esters of the formula (XV) are obtained by reducing the oxo compounds of the formula (XVI) with sodium tetrahydridoborate, if appropriate using a diluent, for example water or aqueous methanol, and if appropriate in the presence of a water-immiscible solvent, for example methylene chloride, at a temperature between −20° and +50° C. (see Chem. Ber. 103, (1970), 2984–2986). For working up, the mixture is extracted with a water-immiscible solvent, for example methylene chloride, the extracts are dried and filtered and the solvent is distilled off from the filtrate under reduced pressure.

Since the formyl-cyclopropane derivatives of the formula (XIII) employed as starting compounds and the styryl-cyclopropane derivatives of the formula (XI) in each case contain asymmetric carbon atoms, the compounds of the formulae (XI) and (XIII) can occur in a corresponding number of stereoisomeric forms. The processes according to the invention relate to the preparation of compounds of the formula (XI) which are obtained either in the form of the individual stereoisomers or as mixtures of stereoisomers.

From the styryl-cyclopropane derivatives of the formula (XI) in which Y represents cyano or carbamoyl, the corresponding carboxylic acid esters of the formula (XI) in which Y represents alkoxycarbonyl are obtained in a known manner, for example by reaction with alcohols, for example methanol or ethanol, in the presence of a mineral acid, for example sulphuric acid, at a temperature between 80° and 200° C. (see DE-OS (German Published Specification) No. 2,831,555).

The compounds of the formula (XI) in which Y represents acetyl can be converted into the corresponding carboxylic acids of the formula (XI) in which Y then represents carboxyl in a known manner, for example by reaction with aqueous sodium hypobromite solution (which, if appropriate, has been produced in situ from bromine and sodium hydroxide solution) if appropriate in the presence of an organic solvent, for example dioxane, at a temperature between −20° and +50° C., (see DE-OS (German Published Specification) No. 2,621,833).

Compounds of the formula (XI) in which Y represents carboxyl or alkoxycarbonyl can be used as intermediate products for the preparation of pyrethroids which have an insecticidal and acaricidal action (see DE-OS (German Published Specification) No. 2,730,515).

EXAMPLES OF PROCESS (1)

Example 1

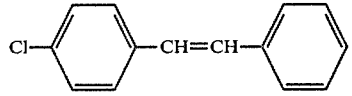
(1)

22.8 g (0.1 mol) of benzylphosphonic acid diethyl ester were added dropwise to a solution, cooled to 0° to 5° C., of 22.4 g (0.2 mol) of potassium tert.-butylate in 100 ml of tetrahydrofuran (dried over sodium) in the course of 15 minutes. The mixture was stirred for one hour; a solution of 28 g (0.1 mol) of α-hydroxy-4-chlorobenzylphosphonic acid diethyl ester in 50 ml of tetrahydrofuran was then added to the mixture, while cooling to 0° to 5° C., and the mixture was stirred at room temperature (about 20° C.) for a further 15 hours. It was then poured into 1 liter of ice-water, filtered off and dried. 18 g (84% of theory) of 1-(4-chlorophenyl)-2-phenyl-ethylene were thus obtained in the form of colorless crystals of melting point 130° C.

Example 2

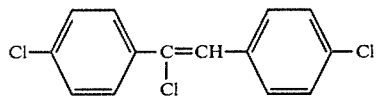
(2)

28 g (0.1 mol) of α-hydroxy-4-chloro-benzyl-phosphonic acid diethyl ester and 30 g (0.1 mol) of α-chloro-4-chloro-benzyl-phosphonic acid diethyl ester were dissolved in 50 ml of toluene and this solution was added dropwise to an intensively stirred mixture of 100 ml of toluene, 100 ml of 40% strength sodium hydroxide solution and 2 g of tetrabutyl-ammonium bromide at an internal temperature of 30° to 35° C. in the course of 30 minutes. The mixture was stirred at room temperature (about 20° C.) for a further 15 hours, the organic phase was separated off, washed twice with water, dried and filtered and the solvent was distilled off from the filtrate in vacuo. The residue was obtained as crystals from ligroin: 14 g (49% of theory) of 1-chloro-1-(4-chlorophenyl)-2-(4-chloro-phenyl)-ethylene; melting point: 89° C.

Example 3

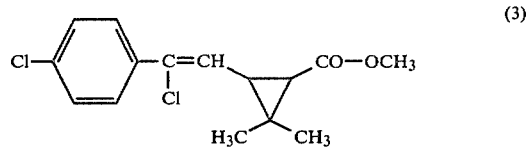
(3)

30 g (0.1 mol) of α-chloro-4-chloro-benzyl-phosphonic acid diethyl ester were added dropwise to a solution, cooled to 0° to 10° C., of 8.8 g (0.2 mol) of sodium methylate in 200 ml of tetrahydrofuran. The mixture was stirred at 0° C. for one hour; a solution of α-hydroxy-α-(3-methoxycarbonyl-2,2-dimethyl-cycloprop-1-yl)-methanephosphonic acid dimethyl ester in 50 ml of tetrahydrofuran was then added to the mixture at 0° to 10° C., the reaction mixture was stirred at room temperature (about 20° C.) for about 15 hours, the solvent was distilled off, the residue was taken up in ligroin, the solution was washed with ice-water, dried and filtered and the filtrate was distilled.

18 g (60% of theory) of 3-(2-chloro-2-(4-chlorophenyl)-vinyl)-2,2-dimethyl-cyclopropane-1-carboxylic acid methyl ester of boiling point 100° C./0.01 mbar were obtained.

Example 4

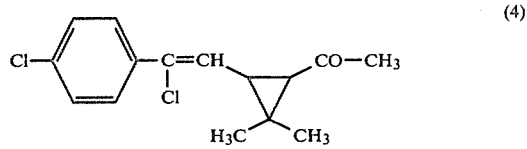
(4)

30 g (0.1 mol) of α-chloro-4-chloro-benzyl-phosphonic acid diethyl ester, dissolved in 50 ml of tetrahydrofuran, were added dropwise to a solution, cooled to 0° to 10° C., of 8.8 g (0.2 mol) of sodium methylate in 200 ml of tetrahydrofuran. The mixture was stirred for one hour; a solution of 25 g (0.1 mol) of α-hydroxy-α-(3-acetyl-2,2-dimethyl-cycloprop-1-yl)-methanephosphonic acid dimethyl ester in 100 ml of tetrahydrofuran was then added to the mixture at 0° to 5° C., the reaction mixture was stirred at 15° to 25° C. for 15 hours, the solvent was distilled off, the residue was taken up in toluene, the toluene mixture was washed three times with water, dried and filtered and the filtrate was distilled.

18 g (64% of theory) of 3-(2-chloro-2-(4-chlorophenyl)-vinyl)-2,2-dimethyl-cycloprop-1-yl methyl ketone of boiling point 90° C./0.01 mbar were obtained.

The following compound was obtained analogously to Example 4:

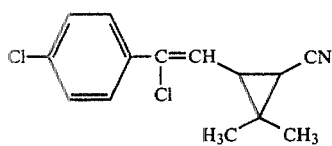
(5)

Boiling point: 94° C./0.01 mbar.

The α-hydroxy-phosphonic acid esters of the formula (II) to be used as starting substances can be prepared, for example, as follows:

EXAMPLE OF PROCESS (3)

Example 5

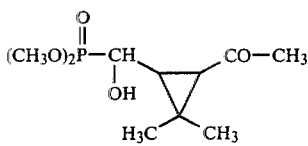
(6)

A solution of 50 g (0.2 mol) of α-oxo-α-(3-acetyl-2,2-dimethyl-cycloprop-1-yl)-methanephosphonic acid dimethyl ester in 50 ml of methylene chloride was added dropwise to a mixture, cooled to 0° to 5° C., of 2.5 g of sodium tetrahydridoborate, 100 ml of water and 100 ml of methylene chloride and the reaction mixture was stirred at 0° to 5° C. for two hours. The aqueous phase was then separated off from the organic phase and was extracted twice more with methylene chloride. The combined organic phases were dried and filtered and the filtrate was evaporated. After recrystallizing the crude product which remained from 200 ml of ethyl acetate/ligroin (2:8), 31 g (62% of theory) of α-hydroxy-α-(3-acetyl-2,2-dimethyl-cycloprop-1-yl)-methanephosphonic acid dimethyl ester of melting point 104° C. were obtained.

The following compounds were obtained analogously:

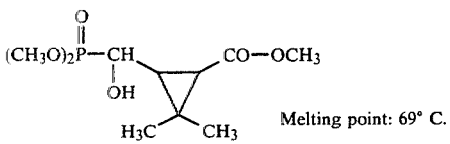
(7)

Melting point: 69° C.

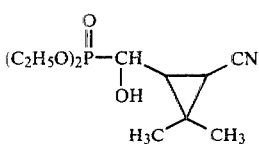
(8)

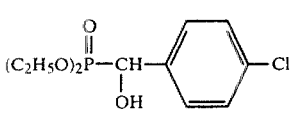
(9)

EXAMPLE OF PROCESS (5)

Example 6

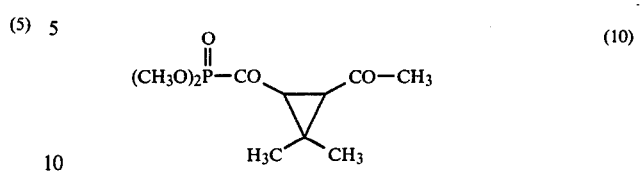
(10)

6.5 g (0.05 mol) of trimethyl phosphite were added dropwise to a solution, warmed to 35° to 40° C., of 9 g (0.05 mol) of 3-acetyl-2,2-dimethyl-cyclopropane-1-carboxylic acid chloride in 20 ml of methylene chloride and the reaction mixture was stirred at 15° to 25° C. for 15 hours. After distilling off the solvent in vacuo, 9 g (72% of theory) of α-oxo-α-(3-acetyl-2,2-dimethyl-cycloprop-1-yl)-methane-phosphonic acid dimethyl ester were obtained.

The following compounds were obtained analogously

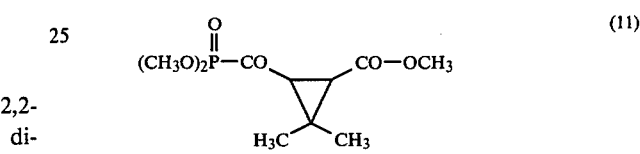
(11)

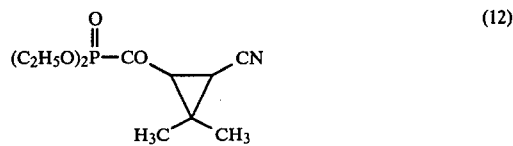
(12)

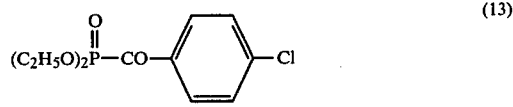
(13)

EXAMPLE OF PROCESS (7)

Example 7

The cyclopropanecarboxylic acids of the formula (VII) to be used as starting substances in process (7) can be prepared, for example, as follows:

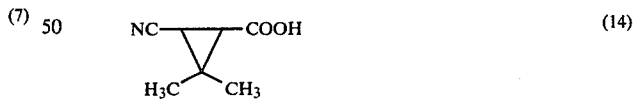
(14)

A suspension of 33.4 g (0.2 mol) of 2-cyano-3,3-dimethyl-cyclopropane-carboxylic acid ethyl ester and 16.8 g (0.3 mol) of potassium hydroxide in 200 ml of water and 100 ml of ethanol was stirred at 20°-25° C. for 15 hours. The alcohol was then stripped off and the aqueous solution was acidified with dilute hydrochloric acid and extracted twice with 100 ml of ether (or methylene chloride) each time. The combined organic extracts were dried over $Na_2SO_4$ and concentrated and the residue was distilled. 21.2 g (76% of theory) of 2-cyano-3,3-dimethyl-cyclopropane-carboxylic acid were obtained in the form of an oil of boiling point 110°-120° C., which crystallized on cooling (melting point: 101°-106° C.).

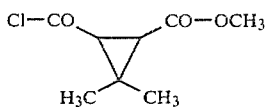

A mixture of 172 g (1 mol) of 3-methoxycarbonyl-2,2-dimethyl-cyclopropane-1-carboxylic acid, 130 g of thionyl chloride, 2 ml of dimethylformamide and 200 ml of methylene chloride was heated to the boil under reflux for four hours. After distillation in vacuo, 135 g (71% of theory) of 3-methoxycarbonyl-2,2-dimethyl-cyclopropane-1-carboxylic acid chloride of boiling point 86° C./15 mbars were obtained.

The following compounds were obtained analogously:

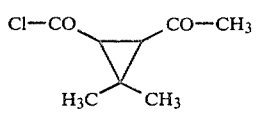

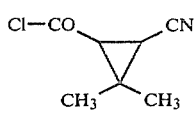

Boiling point: 95–98° C./10 mbars

EXAMPLES OF PROCESS (9)

Example 8

(a) The benzyl-phosphonic acid esters of the formula (XII) to be used as starting substances in process (9) can be prepared, for example, as follows:

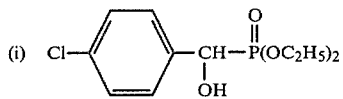

21 g (0.150 mol) of chlorobenzaldehyde were passed into a mixture of 20.7 g (0.15 mol) of diethyl phosphite and 1.09 g (0.0109 mol) of triethylamine at 50°–70° C. in the course of 1 hour, while cooling with water. The reaction batch was subsequently stirred at 70° C. for 1 hour. After cooling, the batch was taken up in 40 g of toluene and the toluene mixture was rinsed several times with dilute hydrochloric acid and cold water. The organic layer was separated off and freed from solvent in vacuo. The solid residue melted at 70°–72° C. The yield was 37 g (88.5% of theory) of 4-chloro-α-hydroxy-benzylphosphonic acid diethyl ester.

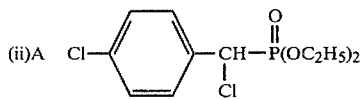

9.2 g (0.0768 mol) of thionyl chloride were added to a mixture of 20.2 g (0.0725 mol) of 4-chloro-α-hydroxybenzylphosphonic acid diethyl ester, 65 g of methylene chloride and 5.8 g (0.0725 mol) of pyridine at 20°–40° C. in the course of about 1 hour, while cooling slightly with water. The reaction mixture was then heated under reflux for 3 hours and subsequently stirred for 12 hours, without further action of heat. The mixture was poured onto about 100 g of ice-water and the organic phase was separated off and dried. After distilling off the solvent, the residue was concentrated under 6 mm Hg and at 45° C. 21 g (97.7% of theory) of 4-chloro-α-chloro-benzylphosphonic acid diethyl ester were obtained as a yellow viscous oil with a purity of 98.6% (gas chromatogram) and a refractive index of $n_D^{24}$: 1.5250.

The following compound was obtained analogously

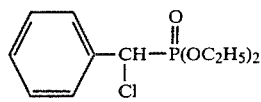

Refractive index: $n_D^{23}$: 1.5117.

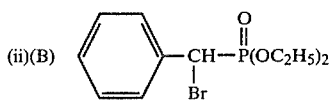

90 g of bromine, dissolved in 250 ml of methylene chloride, were added dropwise to a solution of 131 g (0.5 mol) of triphenylphosphine in 500 ml of methylene chloride at 30°–35° C. with exclusion of moisture. The mixture was subsequently stirred at room temperature for 1 hour, a solution of 122 g (0.5 mol) of α-hydroxy-benzylphosphonic acid diethyl ester in 250 ml of methylene chloride was then added dropwise at −20° C. in the course of 1 hour, the mixture was subsequently stirred at −20° C. for 1 hour and 40 g of pyridine, dissolved in 250 ml of methylene chloride, were then added dropwise at −20° C. in the course of 1 hour. The mixture was subsequently stirred for 20 hours, during which the temperature rose slowly to +20° C.

The reaction mixture was transferred to a pearshaped flask and the solvent was distilled off under a waterpump vacuum. The residue was extracted by stirring with one liter of ether and the undissolved triphenylphosphine oxide was filtered off. (Triphenylphosphine oxide: 120 g=86% of theory). The mother liquor was concentrated in vacuo and the residue was distilled under a high vacuum. 112 g (72% of theory) of α-bromobenzylphosphonic acid diethyl ester were obtained as a light yellow oil with a boiling point of 110° C./0.01 mm Hg and a purity of 95.5% (gas chromatogram).

The following compound was obtained analogously

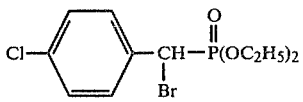

Boiling point: 125° C./0.01 mm Hg.

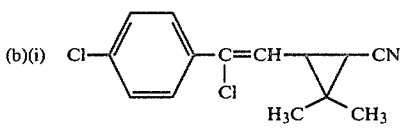

A solution of 11.8 g (0.04 mol) of α-chloro(4-chlorobenzyl)-phosphonic acid diethyl ester in 20 ml of tetrahydrofuran was added dropwise to a solution of 8.9 g (0.042 mol) of sodium methylate in methanol and 80 ml of tetrahydrofuran at 0°–10° C. and the mixture was subsequently stirred at 0°–10° C. for 1 hour. 5 g (0.04 mol) of 3,3-dimethyl-2-cyano-cyclopropanecarbaldehyde were then added at 10° C. and the reaction mixture was subsequently stirred for 1 hour, without further cooling, and then poured onto 300 ml of water. The aqueous solution was extracted three times with 100 ml of methylene chloride each time and the combined organic phases were dried over sodium sulphate and evaporated in vacuo. 9.4 g (89% of theory) of 3,3-dimethyl-2-(2-chloro-2-(4-chlorophenyl)-vinyl)-cyclopropanecarboxylic acid nitrile remained as a yellow oil with the refractive index $n_D^{22}$: 1.5611.

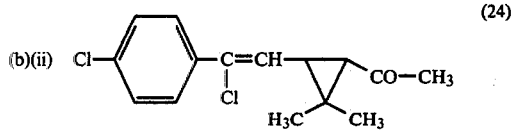

(b)(ii)     (24)

A solution of 23.7 g (0.08 mol) of α-chloro-(4-chlorobenzyl)-phosphonic acid diethyl ester in 40 ml of tetrahydrofuran was added dropwise to a solution of 17.8 g (0.084 mol) of sodium methylate in methanol and 160 ml of tetrahydrofuran at 0°–10° C. and the mixture was subsequently stirred at 0°–10° C. for 1 hour. 11.2 g (0.08 mol) of trans-3,3-dimethyl-2-acetyl-cyclopropanecarbaldehyde were then added at 10° C. and the reaction mixture was subsequently stirred for 2 hours, without further cooling, and then poured onto 800 ml of water. The aqueous solution was extracted three times with 200 ml of methylene chloride each time and the combined organic phases were dried over sodium sulphate and evaporated in vacuo. 19.7 g (87% of theory) of trans-3,3-dimethyl-2-(2-chloro-2-(4-chlorophenyl)-vinyl)-1-acetyl-cyclopropane were thus obtained as a yellow oil with a boiling point of 120°–128° C./0.1 mm/Hg.

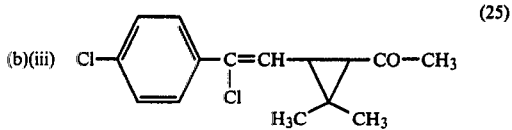

(b)(iii)     (25)

24.1 g (0.09 mol) of α-chloro-(4-chloro-benzyl)phosphonic acid dimethyl ester were added dropwise to a solution of 4.9 g (0.09 mol) of sodium methylate in a mixture of 20 ml of methanol and 200 ml of tetrahydrofuran at 0° C. 12.6 g (0.09 mol) of 3,3-dimethyl-2-acetyl-cyclopropanecarbaldehyde in 50 ml of tetrahydrofuran were then added at 20° C. and the reaction mixture was subsequently stirred for 5 hours.

After working up as in Example 1, 16 g (63% of theory) of 3,3-dimethyl-2-(2-chloro-2-(4-chlorophenyl)-vinyl)-1-acetyl-cyclopropane were obtained in the form of an oil with the refractive index $n_D^{20}$: 1.5698.

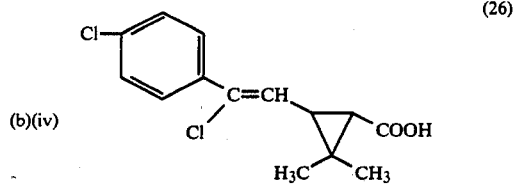

(b)(iv)     (26)

13.8 g of bromine were added dropwise to a solution of 11.5 g of sodium hydroxide in 60 ml of water at 5°–10° C., and a solution of 8.1 g (0.029 mol) of trans-3,3-dimethyl-2-(2-chloro-2-(4-chloro-phenyl)-vinyl)-1-acetylcyclopropane in 30 ml of dioxane was then added dropwise at 0°–5° C. The mixture was subsequently stirred for 3 hours, without cooling, pouredonto 250 ml of water and extracted twice with 50 ml of ether each time. The aqueous phase was freed from adhering ether in vacuo and then brought to pH 2 by adding aqueous hydrochloric acid. After crystallization, the product was filtered off and rinsed with water. 6.2 g (77% of theory) of trans-3,3-dimethyl-2-(2-chloro-2-(4-chlorophenyl)-vinyl)-cyclopropanecarboxylic acid were thus obtained in the form of pale yellow-colored crystals with a melting point of 103°–106° C.

EXAMPLES OF PROCESS (11)

Example 9

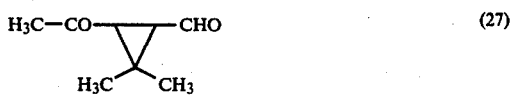

(27)

36.6 g (0.495 mol) of tert.-butanol were added dropwise to a mixture of 6.3 g (0.165 mol) of lithium alanate and 100 ml of tetrahydrofuran at 20°–30° C. in the course of 1 hour. The mixture was subsequently stirred at room temperature for 2 hours and was then added dropwise to a solution of 26.1 g (0.15 mol) of trans-3,3-dimethyl-2-acetyl-cyclopropane-carboxylic acid chloride in 75 ml of tetrahydrofuran at −50° to −60° C. When the addition has ended, the mixture was subsequently stirred for 1 hour, without cooling, poured onto a mixture of 30 ml of concentrated sodium chloride and 300 g of ice and extracted twice by shaking with 400 ml of ether each time. The organic phases were first washed with 50 ml of saturated sodium bicarbonate solution and then with 100 ml of water, dried over sodium sulphate and evaporated in vacuo. Distillation of the residue in vacuo gave 12.7 g (62% of theory) of trans-3,3-dimethyl-2-acetyl-cyclopropane-carbaldehyde in the form of a colorless oil with a boiling point of 80°–86° C./10 mbars.

EXAMPLES OF PROCESS (12)

Example 10

A mixture of 50 g of α-hydroxy-α-(3-acetyl-2,2-dimethyl-cycloprop-1-yl)-methane-phosphonic acid dimethyl ester, 8 g of sodium hydroxide, 60 ml of water and 200 ml of methylene chloride was stirred at room temperature for 90 minutes. The organic phase was separated off, dried, and distilled twice. 20 g (71% of theory) of 3,3-dimethyl-2-acetyl-cyclopropane-carbaldehyde were obtained in the form of a colorless oil of boiling point 78° C./8 mbars.

The following compound was obtained analogously

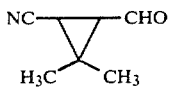
(28)

Boiling point: 77° C./3 mbars.

It will be appreciated that the instant specification and examples are set forth by way of illustration and not limitation, and that various modifications and changes may be made without departing from the spirit and scope of the present invention.

We claim:

1. A process for the preparation of an alkene of the formula

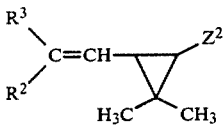

in which
$R^2$ represents hydrogen or halogen,
$R^3$ represents halogen, cyano, an alkyl, alkenyl, alkynyl, cycloalkyl, aralkenyl, aryl, alkylcarbonyl, arylcarbonyl, alkoxycarbonyl or aminocarbonyl radical or
phenyl which carries one or more substituents selected from halogen,
$C_1$-$C_4$-alkyl, $C_1$-$C_2$-halogenoalkyl,
$C_1$-$C_4$-alkoxy, $C_1$-$C_2$-halogenoalkoxy,
$C_1$-$C_4$-alkylthio and $C_1$-$C_2$-halogenoalkylthio, and
$Z^2$ represents cyano, carbamoyl, acetyl or $C_1$-$C_4$-alkoxycarbonyl,
comprising reacting an α-hydroxy-phosphonic acid ester of the formula

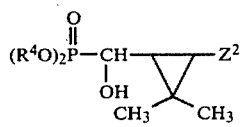

in which
$R^4$ each independently represents alkyl or phenyl, or the two radicals $R^4$ together represent alkylene, with a phosphorus-containing olefinating agent of the formula

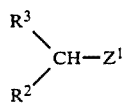

in which
$Z^1$ represents a phosphorus-containing radical

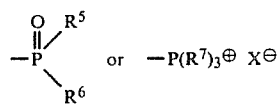

wherein
$R^5$ and $R^6$ are identical or different and individually represent alkyl, phenyl, alkoxy or phenoxy or $R^5$ and $R^6$ together represent alkanedioxy, $R^7$ represents alkyl or phenyl and
X represents halogen, in the presence of a base at a temperature between about −70° and +150° C., the reaction being effected in a water-free inert solvent or in a two-phase medium comprising an aqueous phase and a water-immiscible organic solvent.

2. A process according to claim 1, in which $R^4$ represents methyl or ethyl.

3. A process according to claim 1, in which $R^2$ represents hydrogen, chlorine or bromine,
and $Z^1$ represents the radical

wherein $R^5$ and $R^6$ are identical or different and individually represent $C_1$-$C_4$-alkoxy or phenoxy or together represent 2,2-dimethyl-propane-1,3-dioxy.

4. A process according to claim 1, in which the reaction is effected in the presence of a water-free inert organic solvent.

5. A process according to claim 1, in which the reaction is effected in a two-phase medium comprising an aqueous phase and a water-immiscible organic solvent, and a phase-transfer catalyst is employed.

6. A process according to claim 1, in which the base is an alkali metal hydroxide, an alkali metal alcoholate, an alkali metal hydride or an alkyl-lithium compound.

7. A process according to claim 3, in which $R^4$ represents methyl or ethyl, the α-hydroxy-phosphonic acid ester and phosphorus-containing olefinating agent are reacted in approximately equimolar amounts at a temperature of about −20 to +50° C., the base is an alkali metal hydroxide, an alkali metal alcoholate, an alkali metal hydride or an alkyl-lithium compound, and the reaction is effected in a two-phase medium comprising an aqueous phase, water-immiscible organic solvent and a tetra-alkylammonium salt or a trialkyl-benzyl-ammonium salt as a phase transfer catalyst.

8. A process according to claim 7, in which the α-hydroxy-phosphonic acid ester is produced by reacting a carboxylic acid of the formula

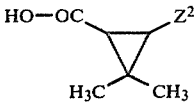

with a chlorinating agent at a temperature between about 20° and 80° C. to produce a carboxylic acid chloride of the formula

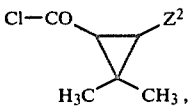

reacting the carboxylic acid chloride at a temperature between about −20° and +150° C. with a phosphorus acid ester of the formula

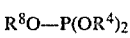

$R^8O$—$P(OR^4)_2$ in which R⁸ represents methyl or ethyl, to produce an α-oxo-phosphonic acid ester of the formula
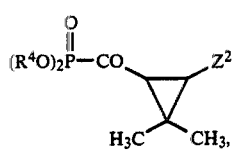
and reacting the α-oxo-phosphonic acid ester at a temperature between about −20° and +50° C. with a hydride complex of the formula
M(M¹H₄)
in which
M represents lithium, sodium or potassium and
M¹ represents boron or aluminum.
* * * * *